(12) United States Patent
Plodinec et al.

(10) Patent No.: US 11,686,720 B2
(45) Date of Patent: Jun. 27, 2023

(54) NANOMECHANICAL PROFILING OF BREAST CANCER MOLECULAR SUBTYPES

(71) Applicant: UNIVERSITAT BASEL, Basel (CH)

(72) Inventors: Marija Plodinec, Basel (CH); Ellen Obermann, Basel (CH); Philipp Oertle, Basel (CH); Christian Räz, Magden (CH)

(73) Assignee: UNIVERSITAT BASEL, Basel (CH)

( * ) Notice: Subject to any disclaimer, the term of this patent is extended or adjusted under 35 U.S.C. 154(b) by 768 days.

(21) Appl. No.: 15/770,205

(22) PCT Filed: Oct. 24, 2016

(86) PCT No.: PCT/EP2016/075587
§ 371 (c)(1),
(2) Date: Apr. 22, 2018

(87) PCT Pub. No.: WO2017/068197
PCT Pub. Date: Apr. 27, 2017

(65) Prior Publication Data
US 2018/0306769 A1   Oct. 25, 2018

(30) Foreign Application Priority Data
Oct. 22, 2015   (EP) .................................. 15191137

(51) Int. Cl.
*G01N 3/42* (2006.01)
*G01N 33/483* (2006.01)
(Continued)

(52) U.S. Cl.
CPC ........... *G01N 33/4833* (2013.01); *G01N 3/00* (2013.01); *G01N 3/068* (2013.01); *G01N 3/42* (2013.01);
(Continued)

(58) Field of Classification Search
CPC ............... G01N 33/4833; G01N 3/068; G01N 33/57415; G01N 33/48; G01N 3/00;
(Continued)

(56) References Cited

U.S. PATENT DOCUMENTS

| | | | | |
|---|---|---|---|---|
| 8,756,711 | B2 * | 6/2014 | Plodinec | G01Q 60/366 850/63 |
| 2005/0239047 | A1 * | 10/2005 | Gimzewski | G01N 33/5091 435/4 |

(Continued)

FOREIGN PATENT DOCUMENTS

| | | |
|---|---|---|
| CN | 101634629 | 1/2010 |
| CN | 102183679 | 9/2011 |

(Continued)

OTHER PUBLICATIONS

Plodinec, et al ("The nanomechanical signature of breast cancer" Nature Nanotechnology, 7. 11 (2012) pp. 757-765) (Year: 2012).*
(Continued)

*Primary Examiner* — Michael Maskell
(74) *Attorney, Agent, or Firm* — JMB Davis Ben-David

(57) ABSTRACT

The invention relates to a method for classifying a tissue sample obtained from mammary carcinoma. The method comprises determining a stiffness value for each of a plurality of points on said tissue sample, resulting in a stiffness distribution, and assigning said sample to a breast cancer subtype and nodal status based on said stiffness distribution.

18 Claims, 11 Drawing Sheets

(51) Int. Cl.
*G01N 33/48* (2006.01)
*G01N 3/00* (2006.01)
*G01N 33/574* (2006.01)
*G01N 3/06* (2006.01)
G01Q 60/36 (2010.01)
G01Q 60/24 (2010.01)

(52) U.S. Cl.
CPC ....... *G01N 33/48* (2013.01); *G01N 33/57415* (2013.01); *G01N 2203/0089* (2013.01); *G01N 2203/0286* (2013.01); *G01N 2291/02827* (2013.01); *G01N 2800/7028* (2013.01); *G01Q 60/24* (2013.01); *G01Q 60/366* (2013.01)

(58) Field of Classification Search
CPC ........... G01N 3/42; G01N 2291/02827; G01N 2203/0089; G01N 2203/0286; G01N 2800/7028; G01Q 60/366; G01Q 60/24
USPC .............................................. 850/21, 33, 63
See application file for complete search history.

(56) References Cited

U.S. PATENT DOCUMENTS

| 2013/0266665 | A1 | 10/2013 | Dorig | |
| 2014/0338073 | A1 | 11/2014 | Plodinec | |
| 2015/0346191 | A1* | 12/2015 | Aneja | G16H 50/30 424/94.5 |

FOREIGN PATENT DOCUMENTS

| CN | 103389392 | 11/2013 |
| CN | 103827889 | 5/2014 |
| WO | 2012076729 | 6/2012 |
| WO | 2014090971 | 6/2014 |

OTHER PUBLICATIONS

Christian Raez et al: "Taking the atomic force microscopy to the clinic: Predicting the prognosis and recurrence of breast cancer by integrating the nanomechanical profiles of primary tumor and its adjacent tissue", Physics of Cancer, Jan. 1, 2014.

Hardik J. Pandya et al: "Accurate characterization of benign cancerous breast tissues: Aspecific patient studies using piezoresistive miscrocantilevers," Biosensors and Bioelectronics, vol. 63, Jan. 1, 2015, pp. 414-424.

I. I. Acerbi et al: "Human breast cancer invasion and aggression correlates with ECM stiffening and immune cell infiltration", Integrative Biology, vol. 7, No. 10, May 1, 2015, pp. 1120-1134.

Max Denis et. al.: "Correlating Tumor Stiffness with Immunohistochemical Subtypes of Breast Cancers: Prognostic Value of Comb-Push Ultrasound Shear Elastography for Differentiating Luminal Subtypes", Plos One, vol. 11, No. 10, Oct. 24, 2016, p. e0165003.

Plodinec, Marija, et al. "The nanomechanical properties of rat fibroblasts are modulated by interfering with the vimentin intermediate filament system." Journal of structural biology 174.3 (2011): 476-484.

Loparic, Marko, et al. "Micro-and nanomechanical analysis of articular cartilage by indentation-type atomic force microscopy: validation with a gel-microfiber composite." Biophysical journal 98.11 (2010): 2731-2740.

Plodinec, Marija, et al. "The nanomechanical signature of breast cancer." Nature nanotechnology 7.11 (2012): 757-765.

Oliver, Warren Carl, and George Mathews Pharr. "An improved technique for determining hardness and elastic modulus using load and displacement sensing indentation experiments." Journal of materials research 7.6 (1992): 1564-1583.

* cited by examiner

Fig. 11

Different Molecular Subtypes of Breastcancer

- Luminal A: Estrogen positive, Progesterone ≥20%, Ki-67 <20%
- Luminal B: Estrogen positive and either Progesterone <20% or Ki-67 ≥20%
- Luminal B-like: Estrogen positive, Her2 positive
- Her2: Estrogen negative, Her2 positive
- Basal: Estrogen, Progesterone and Her2 negative

NANOMECHANICAL PROFILING OF BREAST CANCER MOLECULAR SUBTYPES

CROSS-REFERENCE TO RELATED APPLICATIONS

This is the U.S. National Stage of International Patent Application No. PCT/EP2016/075587 filed on Oct. 24, 2016, which was published in English under PCT Article 21(2), and which in turn claims the benefit of European Patent Application No. 15191137.7 filed on Oct. 22, 2015.

BACKGROUND

Breast cancer is the most frequent occurring malignancy and the second most frequent cause of cancer death in women in developed countries. Yet, while primary tumours are rarely fatal, metastases are responsible for the majority of cancer-related deaths. There are some parameters which serve as prognostic markers for the development of metastases, but despite considerable efforts, it is still not possible to predict accurately an individual's risk. Therefore, adjuvant therapy is frequently administered to patients who might have been cured by surgery and anti-hormonal treatment alone. Current classification of breast cancer—including prognostic and predictive markers—is still mainly based on clinical and histopathological criteria, i.e. patient age, tumour size, lymph node involvement, histological type of the tumour, expression of oestrogen and progesterone receptors, HER2/neu, and Ki-67 and tumour grade.

Yet risk stratification based on only clinical pathological parameters may be misleading. Especially in early, HER2/neu-negative breast cancer (i.e. stages I, IIA, IIB, and IIIA), these clinicopathological factors are not sufficient for clinical decision making particularly regarding adjuvant chemotherapy since substantial over- or undertreatment may occur. Since 2007, international guidelines have recommended to add further tests to the established risk assessment.

The main goal of the research on breast cancer is therefore the development of prognostic markers which are assessed by quality assured certified tests, can be routinely used, and whose costs are acceptable. These markers should help to optimize cancer diagnosis, orientate therapy choice, and support patient follow-up.

However, all currently available tests suffer from certain drawbacks. In general, they are only validated for well-defined subgroups of patients, for example, in node-negative patients with moderately differentiated tumours. In addition, the tests are mostly performed in central institutions, which require time for delivery of the tumour samples to the central laboratory. In addition, there is no local (quality) control over the processing of the sample.

Based on this background, it is therefore the objective of the present invention to provide a reliable and simple method for subtyping breast cancer sample and/or providing prognostic and/or predictive information about breast cancer.

The objective is attained by the subject matter of the independent claim.

Definitions

The terms stiffness, elasticity or contact stiffness in the context of the present specification refers to the resistance of a tissue sample or tissue to deformation by an applied force. The stiffness or elasticity is measured as the elastic modulus of the tissue sample in Pascal (Pa). A soft tissue sample is characterized by a low stiffness value and a rigid tissue is characterized by an elevated stiffness value.

Such deformation force may be applied to the tissue sample or tissue by an intender or stylus (as part, for example, of an atomic force microscope) that impinges the tissue sample or tissue, wherein either the intender or the tissue sample is moved in a vertical direction relative to each other. To measure a plurality of points on a sample, the intender or the sample may be additionally moved in a lateral direction, wherein a lateral direction in the sense of the invention means a direction that is orthogonal to the vertical direction.

The intender or stylus may be a cantilever with a sharp tip or an attached colloidal particle that acts as a probe. A cantilever in the context of the present specification means a beam or arm that is anchored at only one end. Deflections of the cantilever caused by repulsive or attractive forces between the sample surface and the tip may be optically detected, for example by an interferometer or by a laser focused on the cantilever's back, and reflected onto a split photodiode, wherein the photodiode registers the deflection of the cantilever as a voltage difference, which can be converted into nanometres. Alternatively, the deflection of the cantilever may be detected by a piezoelectric sensor, wherein the strain of the cantilever is converted into an electrical charge. Also alternatively, a self-sensing cantilever may be used such as Piezo-Resistive Sensing Active (PRSA) probes, which are for example, silicon cantilevers with an integrated piezo-resistor bridge and a thermal heater. Advantageously, with such cantilevers no laser adjustment is necessary.

The term area in the context of the present specification refers to an area that is defined by a grid of (measurement) points, wherein each point corresponds to indentation footprint of the stylus as described above and each point is not more than 100 µm, preferably 50 µm, 20 µm, 10 µm or 1 µm away from its next point. By way of non-limiting example, an area has a size of 25 µm$^2$, 50 µm$^2$, 100 µm$^2$, 200 µm$^2$, 300 µm$^2$, 400 µm$^2$, 500 µm$^2$, 600 µm$^2$, 750 µm$^2$, 1000 µm$^2$, 5000 µm$^2$ or 10.000 µm$^2$ and the geometrical centre points of two areas are at least 100 µm, 200 µm, 300 µm, 400 µm, 500 µm or 1 mm apart.

Measured force and indentation depth for any given sample depend on the cantilever spring constant and tip radius.

The term spatial resolution in the context of the present specification refers to the minimal distance between two points on a tissue or tissue sample by which the two points can be discriminated regarding their stiffness. A spatial resolution of at least 1 mm, preferably 100 µm, 10 µm or 1 µm means that the maximal distance by which two points still can be discriminated is 1 mm, preferably 100 µm, 10 µm or 1 µm. A spatial resolution of at least 100 µm, preferably 10 µm or 1 µm also encompasses higher resolutions. A resolution higher than 1 µm means two points having a distance smaller than 1 µm still can be discriminated. Examples of resolutions higher than 100 µm are 10 µm and 1 µm. Examples of resolutions higher than 1 µm are 0.5 µm, 0.1 µm and 10 nm.

The term tissue sample in the context of the present specification refers to a tissue sample that comprises contiguous cells and extracellular matrix. Such tissue sample may be obtained by a biopsy or resection.

The term resection specimen in the context of the present specification refers to a sample representing at least a part of an organ or the body that have been removed from the organ or body. A resection specimen may also comprise a whole organ or body part.

The term tissue biopsy sample in the context of the present specification refers to a tissue sample that is obtained by a biopsy and comprises contiguous cells and extracellular matrix.

The term biopsy in the context of the present specification refers to a method for removal of a tissue part or a tissue for examination. Such biopsy may a needle aspiration biopsy, a punch biopsy, a vacuum-assisted core biopsy, a core needle biopsy or a forceps biopsy. The removal may be performed with the help of suitable tools such as a hollow needle, a round sharp knife or a scalpel. A tissue biopsy sample may additionally be obtained by endoscopes or endoscopic methods.

The biopsy procedure may be guided by a suitable method such as ultrasound or CT (X-ray computed tomography), wherein a tumour or a conspicuous lesion can be detected or located.

The term normal tissue in the context of the present specification refers to an ensemble of contiguous cells and extracellular matrix with identically physiological function that are characterized by a normal, controlled growth and normal cellular and extracellular function and structure.

The term tumour in the context of the present specification refers to a neoplasm or a lesion that is formed by an abnormal growth of neoplastic cells. The tumour can be benign, premalignant or malignant. The classification of a tissue biopsy samples from a human mammary carcinoma is preferred. The term benign lesion or tumour in the context of the present specification refers to a tumour that lacks the ability to metastasize.

The term primary tumour in the context of the present specification refers to a tumour originating from the same tissue type as surrounding organ or tissue.

The terms metastasis, metastases or metastasized tumour in the context of the present specification refers to a tumour which has spread from the primary tumour to distant sites such as adjacent tissue, adjacent lymph nodes, axillary lymph nodes or different organs.

The terms malignancy or "a malignant tumour" in the context of the present specification refers to the ability of a tumour to penetrate the basal membrane, invade neighbouring tissues or spread through the body. A malignant tumour is synonymous with a malignant neoplasm or cancer, in particular with invasive cancer.

The term border of the tumour in the context of the present specification is defined as round, smooth, well-defined (mostly in benign tumour) or irregular, poorly defined (often the case in malignant tumours) border between a tumour and adjacent tissue. Histologically is defined as the outermost part of the tumour where tumour cells can be found.

The term adjacent tissue in the context of the present specification is defined as part of the tissue or organ other than tumour. Adjacent tissue is typically surrounding the primary tumour but can be also considered as any part of the tissue of organ without tumour presence.

The term adjacent lymph node or lymph node adjacent to a primary tumour in the context of the present specification particularly refers to lymph node that drains a tumour. Such adjacent lymph nodes are also referred as to sentinel lymph nodes.

The term axillary lymph node in the context of the present specification refers to a lymph node that drains lymph vessels from the lateral quadrants of the breast, the superficial lymph vessels from the walls of the chest and the abdomen above the level of the navel, and the vessels from the upper limb. Axillary lymph nodes are also referred to as armpit lymph nodes.

The term molecular subtype in the context of the present specification refers to defined expression profile or pattern of a breast cancer or mammary tumour, or tumour cells thereof, wherein different subtypes are distinguishable upon the expression profile or pattern of a breast cancer or mammary tumour, or tumour cells thereof.

The term luminal A subtype in the context of the present specification refers to a tumour comprising cancer cells, wherein the cancer cells are positive for the estrogen receptor, at least 20% of the cancer cells of the tumour are positive for the progesterone receptor, and less than 20% of the cancer cells are positive for the protein Ki-67 (UniProt P46013).

The term luminal B subtype in the context of the present specification refers to a tumour comprising cancer cells, wherein the cancer cells are positive for the estrogen receptor, and either less than 20% of the cancer cells of the tumour are positive for the progesterone receptor, or at least 20% of the cancer cells are positive for the protein Ki-67 (UniProt P46013).

The term luminal like B (Her 2+) subtype in the context of the present specification refers to a tumour comprising cancer cells, wherein the cancer cells are positive for the estrogen receptor and the Her2 receptor.

The term basal subtype in the context of the present specification refers to a tumour comprising triple negative cancer cells, wherein the cancer cells are negative for the estrogen receptor, the progesterone receptor and the Her2 receptor.

The term stiffness distribution in the context of the present specification refers to a frequency of different stiffness values determined from an individual tissue biopsy sample. A determined stiffness distribution may additionally be fitted to a Gaussian function. A unimodal stiffness distribution is a distribution of discrete stiffness values having a single maximum, which indicates a sample having a uniform stiffness. A bimodal distribution function has two maxima. Such distribution may be caused by a sample having two differently stiff parts, for example a soft tumour core and a stiff periphery. A trimodal stiffness distribution in the sense of the invention means a distribution characterized by three local maxima. A trimodal distribution may indicate that normal tissue, a border region characterized by hard stroma and a soft tumour core have contributed to the values making up the distribution. A sample at least bimodal stiffness distribution has a bimodal, trimodal or n-modal (with n being an integer >1) distribution function.

The term heterogeneous stiffness distribution in the context of the present specification refers to an n-modal distribution function (with n being an integer >1).

A plurality of stiffness values in the context of the present specification refers to at least 50, 100, 200, 300, 400, 500 900, 1000, 1600, 2500, 3600, 4900, 6400, 8100, 10000, or 21000 stiffness values.

A prognostic marker provides a risk of cancer incidence and/or recurrence or in other words gives an indication of likelihood of disease progression.

A predictive marker provides an indication of patient's response to specific treatment.

The term peak in the context of the present specification refers to a local maximum in the stiffness value distribution and signifies the stiffness value with the highest frequency within a sample, or within the immediate neighboring values.

In the context of the present specification, the term frequency maximum when used with respect to a stiffness value distribution refers to a local or absolute (global) maximum of the graph plotting the frequency of stiffness values over the stiffness values, wherein the frequency maximum is characterized by a frequency value and a stiffness value.

The term physiological conditions in the context of the present specification refers to conditions necessary to preserve the structural integrity and mechanical properties of the biopsy tissue sample, maintaining viability of the tissue by any chemicals or physical agents and include in particular that after collection the sample is stored in a physiological buffer such as phosphate buffered saline, Ringer solution, or transplantation buffer such as Custodiol and stiffness determination is performed at 20, 25, 30 or 37° C. The Ringer solution may further be supplemented with glucose and a protease cocktail. Further, stiffness determination of the biopsy tissue sample may be performed within 1 h, 2 h, 6 h, 12 h, 24 h, 48 h or 72 h after collection without changing the mechanical properties of the sample. "Physiological conditions" particularly do not comprise frozen tissue or thawed tissue, or paraffin-embedded samples.

The term radiation therapy in the context of the present specification particularly refers to the application of ionizing radiation to a tissue that comprises or is suspected to comprise a tumour to control or kill malignant cells.

The term chemotherapy in the context of the present specification particularly refers to the administration of one or more anti-cancer drugs or chemotherapeutic agents to a subject in need thereof, wherein the chemotherapeutic agents may be cytotoxic agents that may reduce the cell division of malignant cells or induce apoptosis in malignant cells. Non-limiting examples for chemotherapeutic agents for treatment of breast cancer include Cyclophosphamide, methotrexate, 5-fluoruracil, doxorubicin or an mTOR inhibitor such as, for example, rapamycin (CAS-No 53123-88-9).

The term hormone therapy or endocrine therapy in the context of the present specification particularly refers to the administration of a compound that modulates the biological activity of human estrogen, human progesteron or their receptors to a subject in need thereof, such as receptor antagonists or receptor inhibitors.

UniProt numbers refer to entries in the UniProt Knowledgebase (UniProtKB).

DESCRIPTION OF THE INVENTION

The present invention is based on the surprising finding that breast cancer tissue samples can be classified into breast cancer subtypes upon their nanomechanical properties.

According to a first aspect of the invention, a method for classifying a tissue sample obtained from a mammary tumour is provided. The method comprises determining a stiffness value for each of a plurality of points on the tissue sample, resulting in a stiffness distribution, resulting in a stiffness distribution, and assigning the sample to a breast cancer molecular subtype based on the determined stiffness distribution.

Advantageously, the method of the invention is more precise, reliable and faster that the presently used state-of-the-art methods such as gene expression profiling or immunohistochemical methods.

In certain embodiments, the stiffness value is determined with a scanning probe microscope, such as for example, an atomic force microscope.

In certain embodiments, the stiffness value is determined with a nanoindenter.

In certain embodiments, the molecular subtype is selected from the group comprised of:
luminal A subtype non-metastasized breast cancer,
luminal B subtype non-metastasized breast cancer,
luminal A subtype metastasized breast cancer,
luminal B subtype metastasized breast cancer,
luminal B like Her2+ subtype metastasized breast cancer,
basal subtype non-metastasized breast cancer, and
basal subtype metastasized breast cancer.

In certain embodiments, a high probability of being a luminal A subtype non-metastasized breast cancer or a luminal B subtype non-metastasized breast cancer is assigned to a sample exhibiting only one frequency maximum between 0.4 kPa and 0.7 kPa in the region below 1 kPa and frequencies in the region between 1.0 kPa and 1.5 kPa, wherein the frequencies are above a threshold, and wherein the threshold equates to the half-maximal frequency of the one frequency maximum between 0.4 kPa and 0.7 kPa (e.g. if the frequency of the frequency maximum between 0.4 kPa to 0.7 kPa ist 100, the frequencies in the region between 1.0 kPa and 1.5 kPa are above 50).

In certain embodiments, a high probability of being a luminal A subtype non-metastasized breast cancer or a luminal B subtype non-metastasized breast cancer is assigned to a sample exhibiting a global frequency maximum between 0.4 kPa and 0.7 kPa in the region below 1 kPa and frequencies in the region between 1.0 kPa and 1.5 kPa, wherein the frequencies are above a threshold, and wherein the threshold equates to the half-maximal frequency of the global frequency maximum between 0.4 kPa and 0.7 kPa (e.g. if the frequency of the frequency maximum between 0.4 kPa to 0.7 kPa ist 100, the frequencies in the region between 1.0 kPa and 1.5 kPa are above 50).

Particularly, a non-metastasized luminal A or luminal B subtype indicates a good prognosis for treatment, a good response to the administered treatment and no administration of a chemotherapy. Additionally, a non-metastasized luminal a or luminal B subtype of breast cancer is characterized by a low risk or probability of recurrence after adequate standard therapy.

Particularly, a non-metastasized luminal A subtype may be treated with compounds that modulates the biological activity of estrogen or its receptor, such as, for example, tamoxifen (CAS-No 10540-29-1), an antagonist of the estrogen receptor, or an aromatase inhibitor such as letrozole (CAS-No. 112809-51-5) or anastrozole (CAS-No 120511-73-1), particularly as adjuvant therapy accompanying surgery.

Particularly, a non-metastasized luminal B subtype may be treated with compounds that modulates the biological activity of progesteron or its receptor. Non-limiting examples include progestins such as megestrol acetate (CAS-No 595-33-5) and medrohydroprogersteron acetate (CAS-No 71-59-9), particularly as adjuvant therapy prior to (neodjuvant) or accompanying surgery.

In certain embodiments, a high probability of being a luminal A subtype metastasized breast cancer is assigned to a sample exhibiting two frequency maximum below 1 kPa and a frequency maximum above 2 kPa. In certain embodiments, a high probability of being a luminal A subtype metastasized breast cancer is assigned to a sample exhibiting two frequency maxima between 0.3 kPa and 0.9 kPa and a frequency maximum above 2 kPa. In certain embodiments, a high probability of being a luminal A subtype metastasized breast cancer is assigned to a sample exhibiting two frequency maximum below 1 kPa and one frequency maximum between 2.0 kPa and 2.5 kPa. In certain embodiments, a high probability of being a luminal A subtype metastasized breast cancer is assigned to a sample exhibiting two frequency maxima between 0.3 kPa and 0.9 kPa and a frequency maximum between 2.0 kPa and 2.5 kPa. In certain embodiments, a high probability of being a luminal A subtype metastasized breast cancer is assigned to a sample exhibiting frequency maxima at 0.375 kPa and 0.875 kPa and a frequency maximum above 2 kPa. In certain embodiments, a high probability of being a luminal A subtype metastasized breast cancer is assigned to a sample exhibiting frequency maxima at 0.375 kPa and 0.875 kPa and a frequency maximum between 2.0 kPa and 2.5 kPa. In certain embodiments, a high probability of being a luminal A subtype metastasized breast cancer is assigned to a sample exhibiting frequency maxima at 0.375 kPa and 0.875 kPa and a frequency maximum at 2.075 kPa. In certain embodiments, a high probability of being a luminal A subtype metastasized breast cancer is assigned to a sample exhibiting two frequency maximum below 1 kPa and a frequency at 2.075 kPa. In certain embodiments, a high probability of being a luminal A subtype metastasized breast cancer is assigned to a sample exhibiting two frequency maxima between 0.3 kPa and 0.9 kPa and a frequency at 2.075 kPa. Particularly, such tissue sample as described above signifies a tumour that has very likely spread to adjacent lymph nodes or axillary lymph nodes.

Particularly, a metastasized luminal A subtype indicates mediocre to poor prognosis and the administration of a chemotherapy, particularly the administration of compounds that modulates the effect of estrogen such as tamoxifen (CAS-No 10540-29-1), an antagonist of the estrogen receptor, or an aromatase inhibitor such as letrozole (CAS-No. 112809-51-5) or anastrozole (CAS-No 120511-73-1), particularly as an adjuvant therapy accompanying surgery and/or radiation therapy. Particularly, a metastasized luminal A subtype is characterized by a high risk or probability of recurrence after adequate standard therapy.

In certain embodiments, a high probability of being a luminal B subtype metastasized breast cancer is assigned to a sample exhibiting a frequency maximum below 0.25 kPa. In certain embodiments, a high probability of being a luminal B subtype metastasized breast cancer is assigned to a sample exhibiting one frequency maximum between 0.1 kPa and 0.25 kPa, particularly at 0.2 kPa. In certain embodiments, a high probability of being a luminal B subtype metastasized breast cancer is assigned to a sample exhibiting one frequency maximum below 0.25 kPa, particularly between 0.1 kPa and 0.25 kPa, more particular at 0.2 kPa, and a frequency maximum between 1.4 kPa and 1.6 kPa. Particularly, such tissue sample as described above signifies a tumour that has very likely spread to adjacent lymph nodes or axillary lymph nodes.

Particularly, a metastasized luminal B subtype tumour indicates a poor prognosis and the administration of chemotherapy. Particularly, a metastasized luminal B subtype is characterized by a high risk or probability of recurrence after adequate standard therapy. Particularly, a metastasized luminal B subtype may be treated with radiation therapy and/or an inhibitor of mTOR, PI3K or IGFR-1, particularly as adjuvant therapy prior to (neodajuvant) or accompanying radiation therapy and/or surgery.

In certain embodiments, a high probability of being a luminal B like Her2+ subtype metastasized breast cancer is assigned to a sample exhibiting a frequency maximum between 0.25 kPa and 0.4 kPa and a frequency maximum between 1.7 kPa and 2.0 kPa. In certain embodiments, a high probability of being a luminal B like Her2+ subtype metastasized breast cancer is assigned to a sample exhibiting a frequency maximum at 0.3 kPa and a frequency maximum between 1.7 kPa and 2.0 kPa. Particularly, such tissue sample as described above signifies a tumour that has very likely spread to adjacent lymph nodes or axillary lymph nodes.

Particularly, a metastasized luminal B like Her2+ subtype indicates a poor prognosis and the administration of a chemotherapy, particularly the administration of compounds such as trastuzumab (also known as Herceptin; CAS-No. 180288-69-1). Particularly, a metastasized luminal B like Her2+ subtype is characterized by a high risk or probability of recurrence after adequate standard therapy. Particularly, a metastasized luminal B like Her2+ subtype may be treated with radiation therapy, particularly as adjuvant therapy accompanying surgery and/or chemotherapy.

In certain embodiments, a high probability of being a basal subtype non-metastasized breast cancer is assigned to a sample exhibiting only one frequency maxima between 0.5 kPa and 0.7 kPa in the region below 1 kPa and frequencies in the region between 1.0 kPa and 1.5 kPa, wherein the frequencies are below a threshold, and wherein the threshold equates to the half-maximal frequency of said one frequency maximum between 0.5 kPa and 0.7 kPa (e.g. if the frequency of the frequency maximum between 0.5 kPa and 0.7 kPa ist 100 the frequencies in the region between 1.0 kPa and 1.5 kPa are below 50).

Particularly, a non-metastasized basal subtype indicates a poor prognosis. Particularly, a non-metastasized basal subtype is characterized by a low risk or probability of recurrence after adequate standard therapy. Particularly, a metastasized basal subtype may be treated with chemotherapy, particularly as adjuvant therapy accompanying surgery or as neoadvjuvant therapy prior to surgery.

In certain embodiments, a high probability of being a basal subtype metastasized breast cancer is assigned to a sample exhibiting two frequency maxima below 1 kPa and that is further characterized by the absence of further frequency maxima above 1.3 kPa. In certain embodiments, a high probability of being a basal subtype metastasized breast cancer is assigned to a sample exhibiting two frequency maxima between 0.2 kPa and 1.0 kPa and that is further characterized by the absence of further frequency maxima above 1.3 kPa. In certain embodiments, a high probability of being a basal subtype metastasized breast cancer is assigned to a sample exhibiting two frequency maxima at 0.3 kPa and 0.9 kPa and that is further characterized by the absence of further frequency maximums above 1.3 kPa. Particularly, such tissue sample as described above signifies a tumour that has very likely spread to adjacent lymph nodes or axillary lymph nodes.

Particularly, a metastasized basal subtype indicates a very poor prognosis. Particularly, a metastasized basal subtype is characterized by a high risk or probability of recurrence after adequate standard therapy. Particularly, a metastasized basal subtype may be treated with radiation therapy, particularly as adjuvant therapy accompanying surgery or chemotherapy. Particularly, a metastasized basal subtype may be treated with chemotherapy, particularly as neoadjuvant therapy prior to surgery.

According to an alternative to the above first aspect of the invention, a method for classifying a tissue sample obtained from a mammary tumour is provided, wherein the method comprises determining a stiffness value for each of a plurality of points on the tissue sample, resulting in a stiffness distribution, resulting in a stiffness distribution, and assigning the sample to a breast cancer molecular subtype based on the determined stiffness distribution, wherein the classes of the classification schema are:

luminal A subtype non-metastasized breast cancer,
luminal B subtype non-metastasized breast cancer,
luminal A subtype metastasized breast cancer,
luminal B subtype metastasized breast cancer,
luminal B like Her2+ subtype metastasized breast cancer,
basal subtype non-metastasized breast cancer, and/or
basal subtype metastasized breast cancer, wherein a high probability of being a luminal A subtype non-metastasized breast cancer or a luminal B subtype non-metastasized breast cancer is assigned to a sample exhibiting only one frequency maximum between 0.4 kPa and 0.7 kPa in the region below 1 kPa and frequencies in the region between 1.0 kPa and 1.5 kPa, wherein the frequencies are above a threshold, and wherein the threshold equates to the half-maximal frequency of said one frequency maximum between 0.4 kPa and 0.7 kPa, a high probability of being a luminal A subtype metastasized breast cancer is assigned to a sample exhibiting two frequency maxima below 1 kPa and a frequency maximum above 2 kPa, a high probability of being a luminal B subtype metastasized breast cancer is assigned to a sample exhibiting a frequency maximum below 0.25 kPa, a high probability of being a luminal B like subtype metastasized breast cancer is assigned to a sample exhibiting a frequency maximum between 0.25 kPa and 0.4 kPa and a frequency maximum between 1.7 kPa and 2.0 kPa, a high probability of being a basal subtype non-metastasized breast cancer is assigned to a sample exhibiting only one frequency maxima between 0.5 kPa and 0.7 kPa in the region below 1 kPa and frequencies in the region between 1.0 kPa and 1.5 kPa, wherein the frequencies are below a threshold, and wherein the threshold equates to the half-maximal frequency of said one frequency maximum between 0.5 kPa and 0.7 kPa, a high probability of being a basal subtype metastasized breast cancer is assigned to a sample exhibiting two frequency maxima below 1 kPa and that is further characterized by the absence of further frequency maxima above 1.3 kPa, and/or a high probability of being a luminal B subtype metastasized breast cancer is assigned to a sample exhibiting two frequency maxima below 1 kPa and a frequency maximum between 1.4 kPa and 2.0 kPa.

In certain embodiments, the tissue sample is a tissue biopsy sample or a resection specimen.

In certain embodiments, a high probability of being a luminal B subtype metastasized breast cancer is assigned to a sample exhibiting two frequency maxima below 1 kPa and a frequency maximum between 1.4 kPa and 2.0 kPa. Particularly, such tissue sample as described above signifies a tumour that has very likely spread to the vascular system.

In certain embodiments, the pluralities of points are determined with a spatial resolution of at least 100 µm, 50 µm, 20 µm, 10 µm or 1 µm.

In certain embodiments, the tissue sample comprises at least a part of the core of the mammary tumour and at least a part of the periphery of the mammary tumour.

In certain embodiments, the tissue sample represents at least one half of the cross-section of the mammary tumour and exhibiting a distinct orientation from core to periphery of the mammary tumour.

In certain embodiments, the tissue biopsy sample is a cylindrical or prismatic biopsy.

In certain embodiments, the plurality of points is arranged within an area or a line.

In certain embodiments, the plurality of points is arranged as a grid of $n_1$ by $n_2$ points, the grid defining an area, wherein $n_1$ and $n_2$ are independently from each other integers>1.

In certain embodiments, the plurality of points is irregularly arranged within the grid or within the area.

In certain embodiments, the plurality of points is determined along a line on the surface of the tissue sample, wherein particularly the line is parallel to the longitudinal axis of the tissue sample, particularly of the tissue biopsy sample, and wherein particularly the points of the plurality are homogeneously or evenly distributed along the line. In certain embodiments, the line extends over at least one quarter, one half or three quarters of longitudinal axis of the tissue sample. In certain embodiments, the line extends over the whole longitudinal axis of the tissue sample. In certain embodiments, the line is a straight line or a sinuous or serpentine line. In certain embodiments, the line has a width of at least two points, particularly 2 to 10 points. In certain embodiments, several lines of indentation curves are measured across the whole sample (5 mm to 15 mm), measuring 5000 to 20'0000 force curves at a spacing ranging from 0.25 µm to 6 µm.

In certain embodiments, a grid of 5 by 5 points (resulting in 25 points), 7 by 7 points, 10 by 10 points, 15 by 15 points, 20 by 20 points, 50 by 50 points or 100 by 100 points are measured for one area. In certain embodiments, the area is defined of a grid of 24×24 points with a size of 400 µm$^2$.

In certain embodiments, the stiffness values of at least two different areas of the same sample are determined, and the distance between the geometrical centres of the areas is 100 µm to 1 cm. In certain embodiments, the distance between the geometrical centres of the areas is 1 mm to 5 mm. In some embodiments, the distance between the geometrical centres of the areas is 5 mm to 10 mm. In some embodiments, the distance between the geometrical centres of the areas is 10 mm to 100 mm. In some embodiments, the distance between the geometrical centres of the areas is 100 mm to 500 mm. In certain embodiments, the stiffness values of at least two different areas of the same sample are determined, and the distance between the geometrical centres of the areas is 100 µm to 1 mm.

In certain embodiments, the stiffness values of at least two different areas of the same sample are determined, and the distance between the geometrical centres of the areas is a multiple of the spatial resolution, said multiple being at least 10 times the spatial resolution. In certain embodiments, the multiple is 20, 30 or 50.

In certain embodiments, the areas of the tissue sample are positioned on the surface of the sample along the sample's longitudinal axis over a distance of 1 mm, 2 mm, 3 mm, 4 mm, 5 mm, 6 mm, 7 mm, 8 mm, 9 mm, 10 mm, 15 mm or 20 mm.

In certain embodiments, the plurality of points comprises stiffness value in the range of 50 to 21000. In certain embodiments, the plurality of points comprises stiffness value in the range of 100 to 21000. In certain embodiments, the plurality of points comprises stiffness values in the range of 400 to 21000. In certain embodiments, the plurality of points comprises stiffness values in the range of 900 to 10000. In certain embodiments, the plurality of points comprises stiffness values in the range 1000 to 8100. In certain embodiments, the plurality of points comprises stiffness values in the range 1600 to 6400. In certain embodiments, the plurality of points comprises stiffness values in the range 2500 to 4900. In certain embodiments, the plurality of points comprises stiffness values in the range 3600 to 4900. In certain embodiments, the plurality of points comprises 50, 100, 400, 900, 1000, 1600, 2500, 3600, 4900, 6400, 8100, 10000 or 21000 stiffness values.

In certain embodiments, the tissue biopsy sample is a cylindrical or prismatic biopsy with a diameter of at least 7 µm. In certain embodiments, the biopsy tissue sample is a cylindrical or prismatic biopsy with a diameter of at least 0.5 mm.

In certain embodiments, the stiffness values are determined under physiological conditions.

In certain embodiments, the plurality of points is recorded within 6 minutes to 6 hours.

In certain embodiments, the plurality of points is recorded at a range of rates from 1000 loading cycles per second to 0.1 loading cycles per second. In certain embodiments, the plurality of points is recorded at a range of rates from 1000 loading cycles per second to 100 loading cycles per second. In certain embodiments, the plurality of points is recorded at a range of rates from 100 loading cycles per second to 10 loading cycles per second. In certain embodiments, the plurality of points is recorded at a range of rates from 10 loading cycles per second to 0.1 loading cycles per second.

In certain embodiments, the plurality of points is recorded with maximum loads ranging from 200 pN to 3 mN, particularly from 0.2 nN to 20 nN.

In certain embodiments, the plurality of points is recorded using an indenter or intenders ranging in stiffness from 2 mN/m to 20 N/m. In certain embodiments, the plurality of points is recorded using an indenter or intenders ranging in stiffness from 2 mN/m to 200 mN/m. In certain embodiments, the plurality of points is recorded using an indenter or intenders ranging in stiffness from 200 mN/m to 2 N/m.

In certain embodiments, the method of the invention further comprises determination, particularly detection or quantification, of a marker on or comprised within the tissue sample, wherein the surface marker is selected from the group comprised of human estrogen receptor (surface marker, UniProt. P03372);
human progesterone receptor (surface marker, UniProt. P06401);
HER2/neu receptor (surface marker, UniProt. P0426), and antigen Ki-67.

According to another aspect of the invention, a system for classifying a tissue sample obtained from mammary carcinoma is provided. The system comprises a device, particularly an atomic force microscope, for determining stiffness values with a resolving power of at least 1 µm (1 µm or less) in terms of spatial resolution and/or of at least 1 kPa (1 kPa or less) in terms of stiffness values and corresponding hardness values,
a programmed integrated circuit,
wherein the programmed integrated circuit is equipped and designated or configured to run the method of the invention.

In certain embodiments, the programmed integrated circuit is comprised within or is a programmed microprocessor that is equipped and designated or configured to run the method of the invention.

According to a further aspect of the invention, a method for treating breast cancer is provided, wherein the method comprises, providing a tissue sample from a mammary tumour of a subject,
assigning the tissue sample to a breast cancer subtype by the method of the invention,
administering a treatment to the subject based on the determined subtype.

In certain embodiments, a hormone or endocrine therapy is administered to the subject in case of the mammary tumour has been classified as luminal A subtype non-metastasized breast cancer or luminal B subtype non-metastasized breast cancer.

In certain embodiments, a compound that modulates the effect of estrogen or its receptor is administered to the subject in case of the mammary tumour has been classified as luminal A non-metastasized subtype breast cancer, wherein particularly the compound is an antagonist of the estrogen receptor, such, as for example, tamoxifen (CAS-No 10540-29-1), or an aromatase inhibitor such as, for example, letrozole (CAS-No. 112809-51-5) or anastrozole (CAS-No 120511-73-1).

In certain embodiments, a compound that modulates the effect of progesteron or its receptor is administered to the subject in case of the mammary tumour has been classified as luminal B subtype non-metastasized breast cancer, wherein particularly the compound is progestine such as, for example megestrol acetate (CAS-No 595-33-5) or medrohydroprogersteron acetate (CAS-No 71-59-9).

In certain embodiment, chemotherapy is administered to the subject in case of the mammary tumour has been classified as basal metastasized or non-metastasized breast cancer, particularly as adjuvant therapy accompanying surgery, particularly before (neoadjuvant) or after surgery. Particularly, such chemotherapy is beneficial to reduce the risk of breast cancer recurrence in the subject.

In certain embodiment, chemotherapy, particularly as adjuvant therapy in combination with hormone therapy and/or surgery, is administered to the subject in case of the mammary tumour has been classified as luminal A subtype metastasized breast cancer or luminal B subtype metastasized breast cancer. Particularly, such chemotherapy is beneficial to reduce the risk of breast cancer recurrence in the subject.

In certain embodiments, radiation therapy is administered to the subject in case of the mammary tumour has been classified as luminal A subtype metastasized breast cancer, luminal B subtype metastasized breast cancer, luminal B like Her2+ subtype metastasized breast cancer, or basal subtype metastasized breast cancer, particularly as adjuvant therapy accompanying surgery, particularly before or after surgery. Particularly, such radiation therapy is beneficial to reduce the risk of breast cancer recurrence in the subject.

In certain embodiments, trastuzumab (also known as Herceptin; CAS-No. 180288-69-1) is administered to the subject in case of the mammary tumour has been classified as luminal B like Her2+ subtype metastasized breast cancer, particularly in combination with radiation therapy and/or surgery.

In certain embodiments, an inhibitor of mTOR (such as for example, rapamycin) or PI3K (Phosphatidylinositol-4, 5-bisphosphate 3 kinase or IGFR-1 (insulin-like growth factor 1 receptor) is administered to the subject in case of the mammary tumour has been classified as luminal B like Her2+ subtype metastasized breast cancer, particularly in combination with radiation therapy and/or surgery.

In certain embodiments, an inhibitor of mTOR (such as for example, rapamycin) or PI3K (Phosphatidylinositol-4, 5-bisphosphate 3 kinase or IGFR-1 (insulin-like growth factor 1 receptor) is administered to the subject in case of the mammary tumour has been classified as luminal B subtype metastasized breast cancer, particularly in combination with radiation therapy, hormone therapy and/or surgery.

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

SHORT DESCRIPTION OF THE FIGURES

FIG. 1 shows normalized histograms representing the nanomechanical profile of mammary tumours (biopsy samples) of Basal N0 (n=1) and N+ (n=2) patients. N0 patients show a very distinct cancer peak at 0.625 kPa whereas N+ patients peak at 0.525 kPa but with a much broader stiffness distribution. In addition, N0 patients have stiffer components than N+ patients. N0 stands for pN0 in TNM-grading, meaning that the primary tumour has not progressed to involve regional lymph nodes. N+ stands for pN1 or higher in TNM-grading, meaning that the primary tumour has progressed to involve regional lymph nodes.

FIG. 2 shows normalized histograms (same area) representing the nanomechanical profile of mammary tumours (biopsy samples) of Luminal A N0 (n=5) and Luminal A N+ (n=3). LumA N+ patients show a more heterogeneous stiffness distribution than Lum N0 patients. LumA N0 patients show prominent peaks 0.575 kPa and 1.425 kPa where N+ patients lack these peaks. In contrast, N+ patients show strong signals at 0.375 kPa, 0.875 kPa and 2.075 kPa which are not dominant in N0 patients. In the cancer region below 1 kPa, LumA N0 is more homogeneous (1 peak at 0.575 kPa) than LumA N+ (2 peaks, 0.375 kPa and 0.875 kPa).

FIG. 3 shows normalized histograms (same area) representing the nanomechanical profile of mammary tumours (biopsy samples) of LumB N0 (n=5) and LumB N+ (n=7). LumB N0 show a more heterogeneous stiffness distribution than N+ patients, there is a higher contribution in the stiff part above 2 kPa. The soft part of LumB N+ is significantly softer than the soft part of LumB N0.

Figure 1:
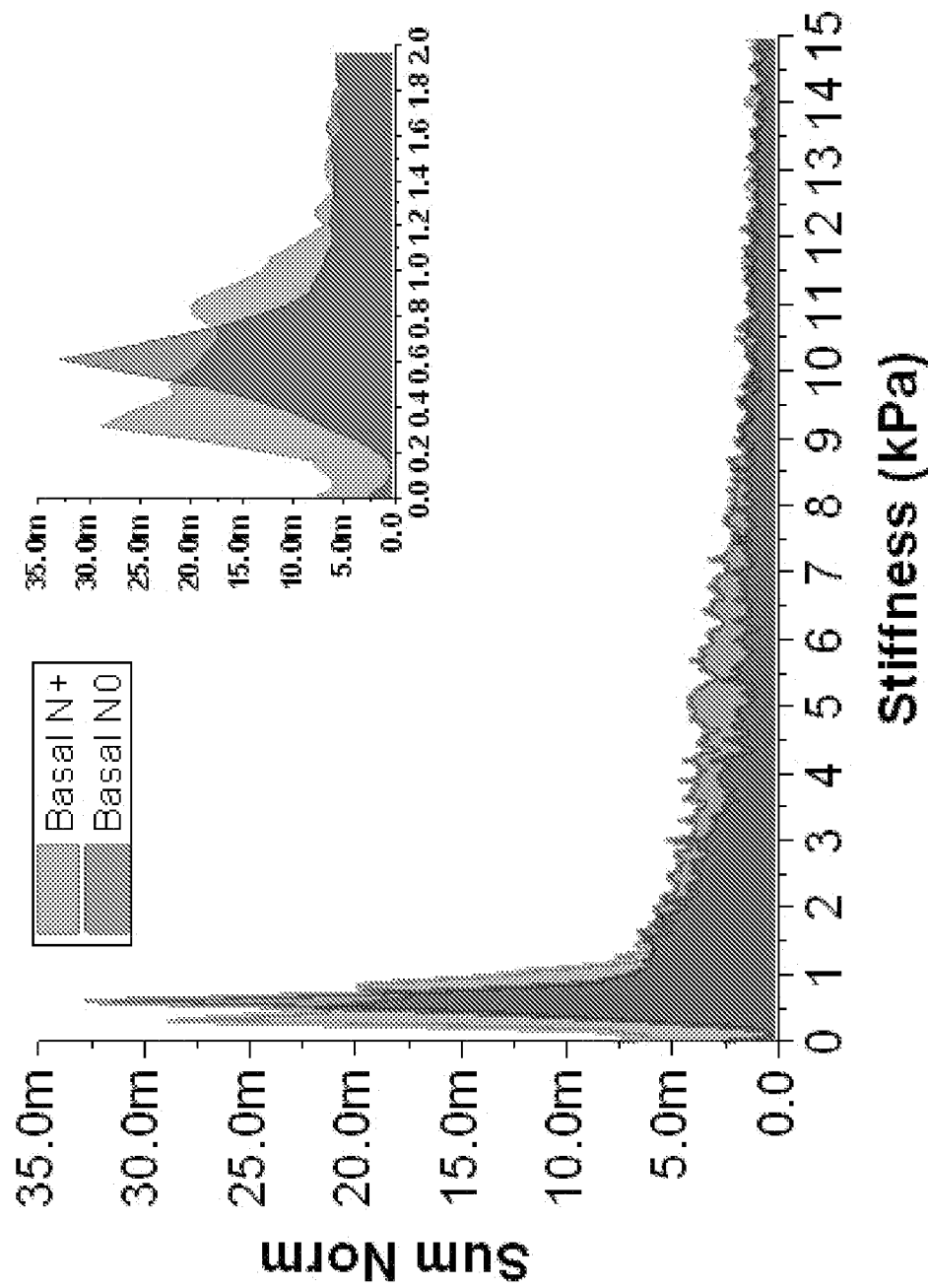
Figure 2:
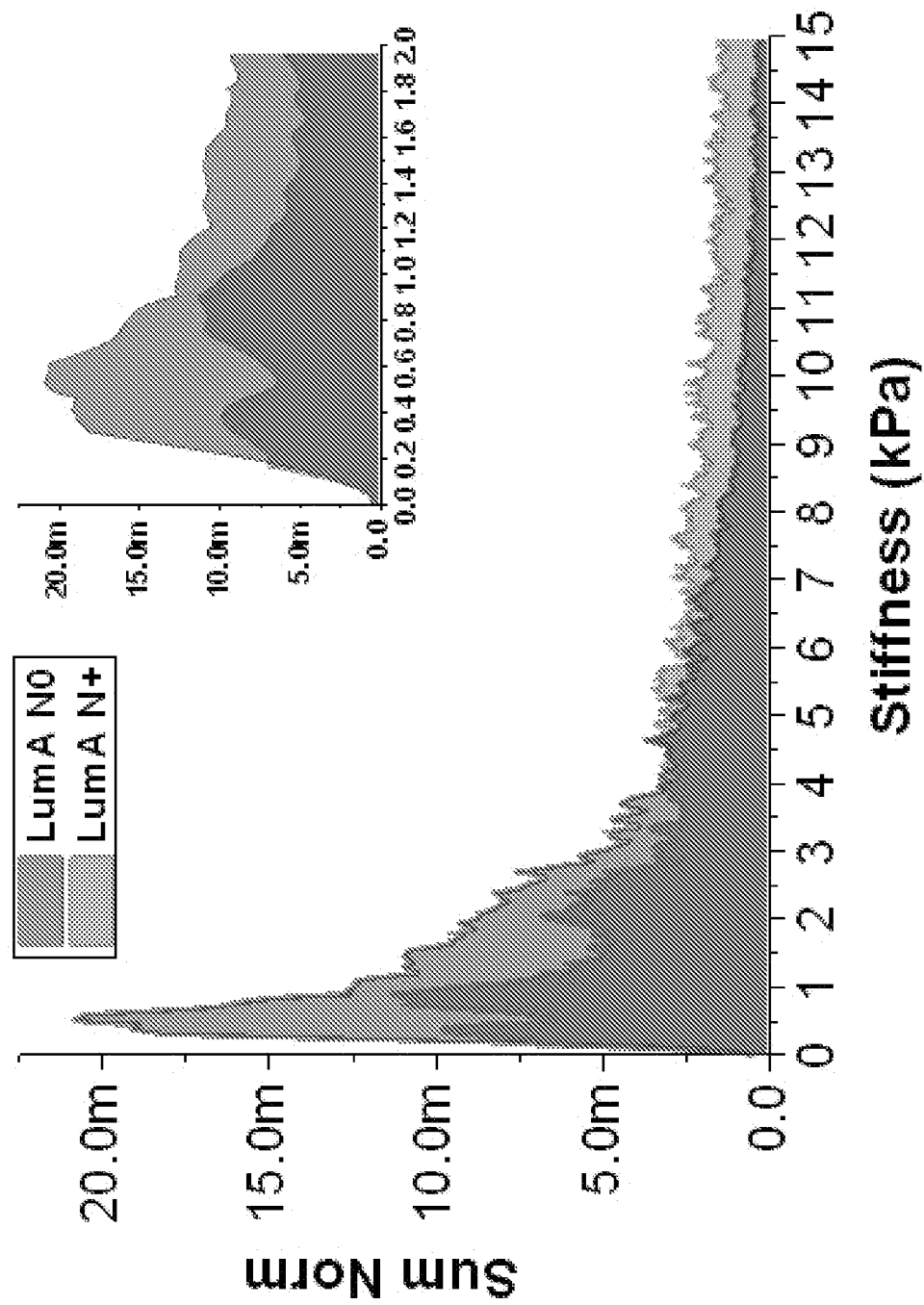
Figure 3:
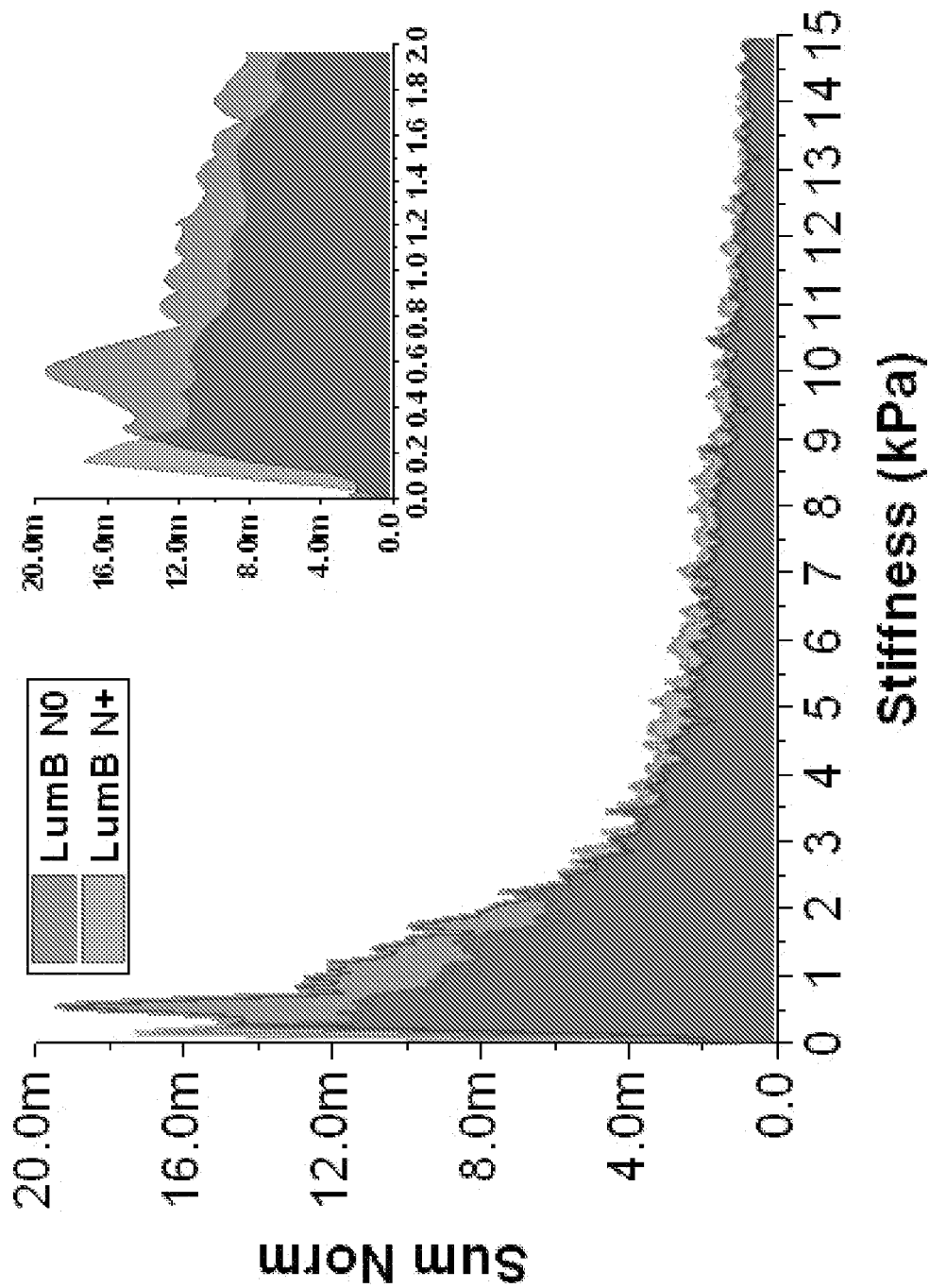
Figure 4:
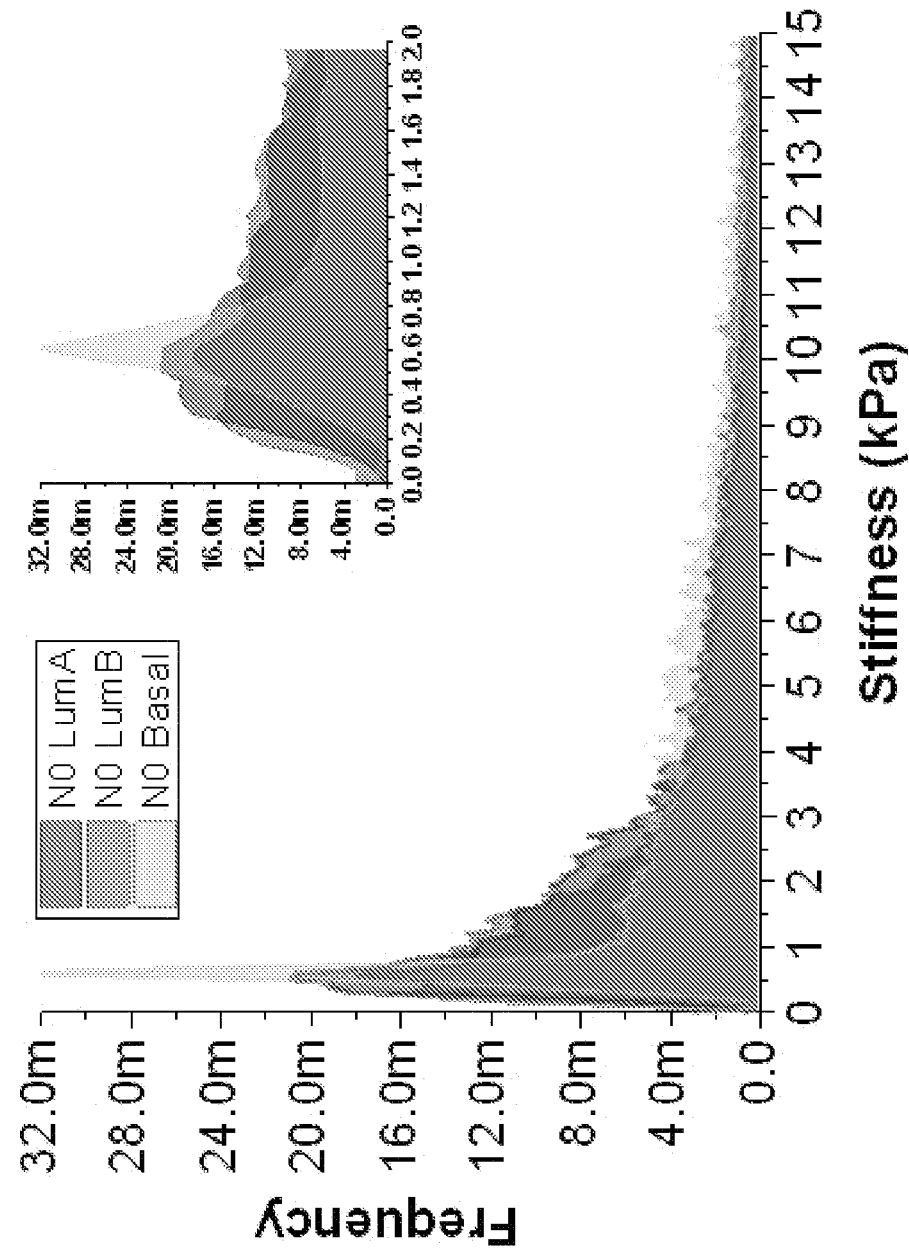
FIG. 4 shows normalized histograms representing the nanomechanical profile of mammary tumours (biopsy samples) of N0: Luminal A (n=5), Luminal B (n=5) and Basal (n=1) patients.
Figure 5:
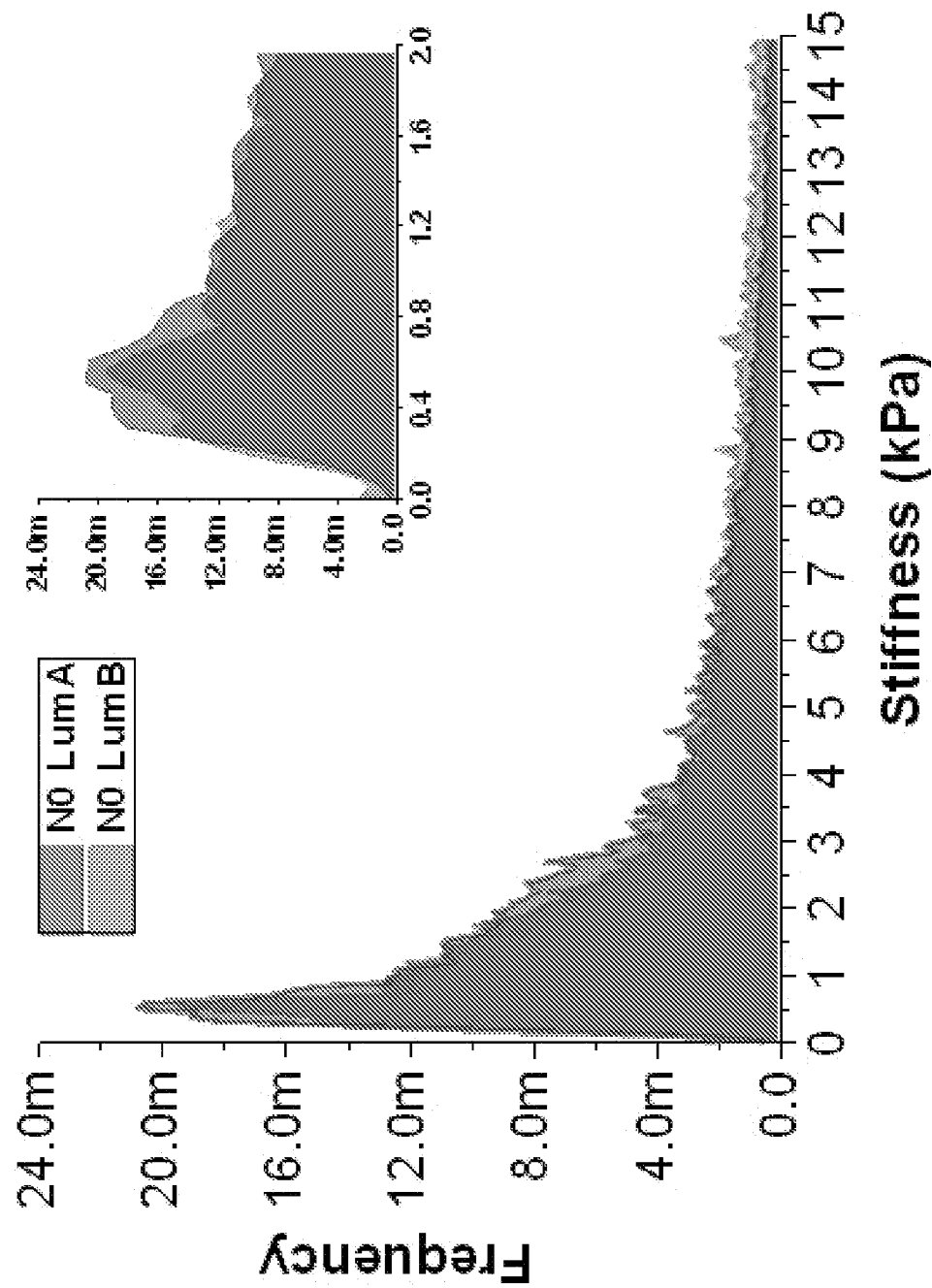
FIG. 5 shows normalized histograms representing the nanomechanical profile of the primary tumours (biopsy samples) of N0 LumA (n=5) and LumB (n=5) patients. The two histograms are very similar, in both cases the cancer area peaks at 0.575 kPa but the peaks are not very distinct, the distribution is very broad.
Figure 6:
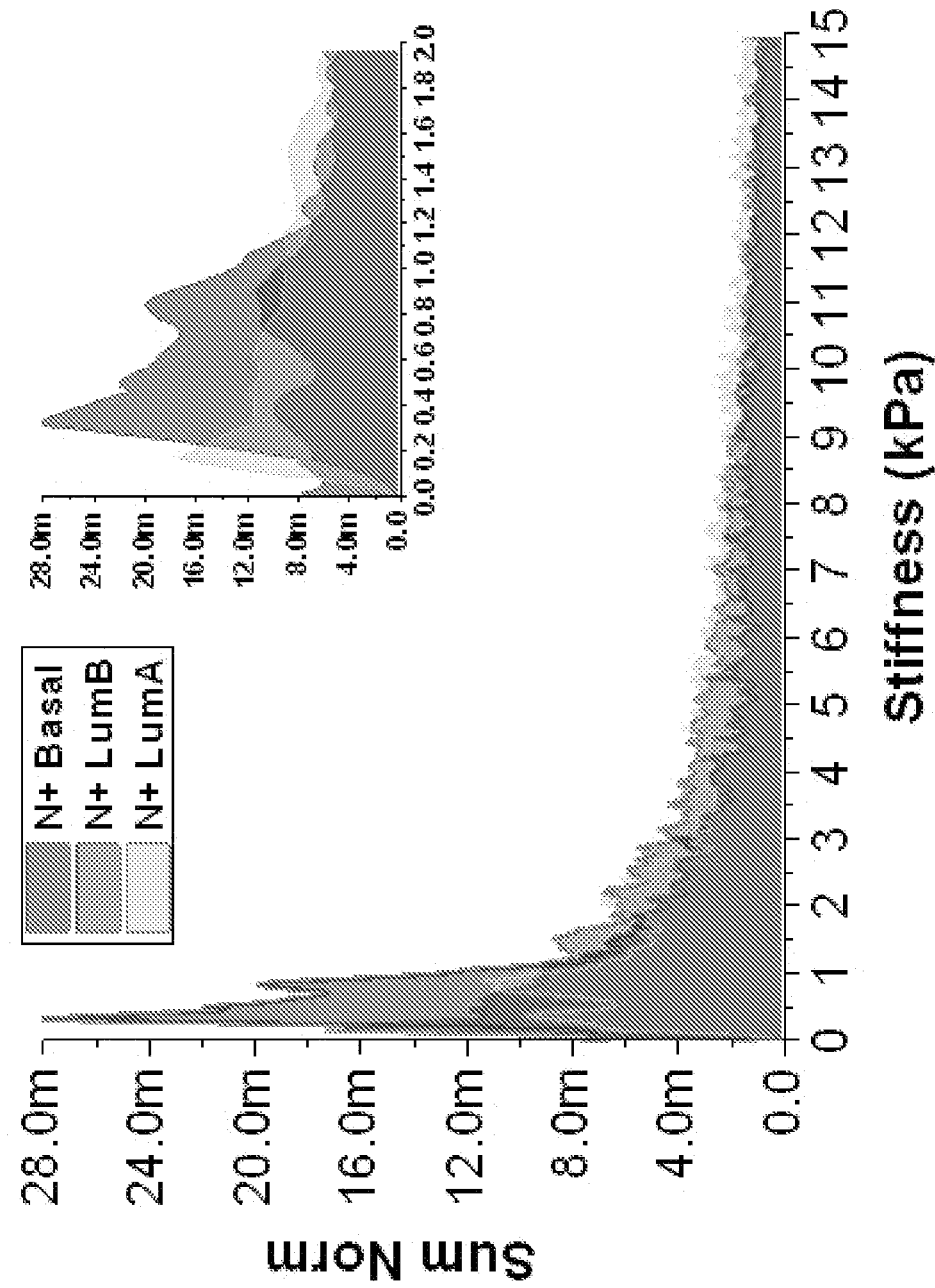
FIG. 6 shows normalized histograms representing the nanomechanical profile of mammary tumours (biopsy samples) of N+: Basal (n=2), Luminal A (n=3) and Luminal B (n=7) patients.
Figure 7:
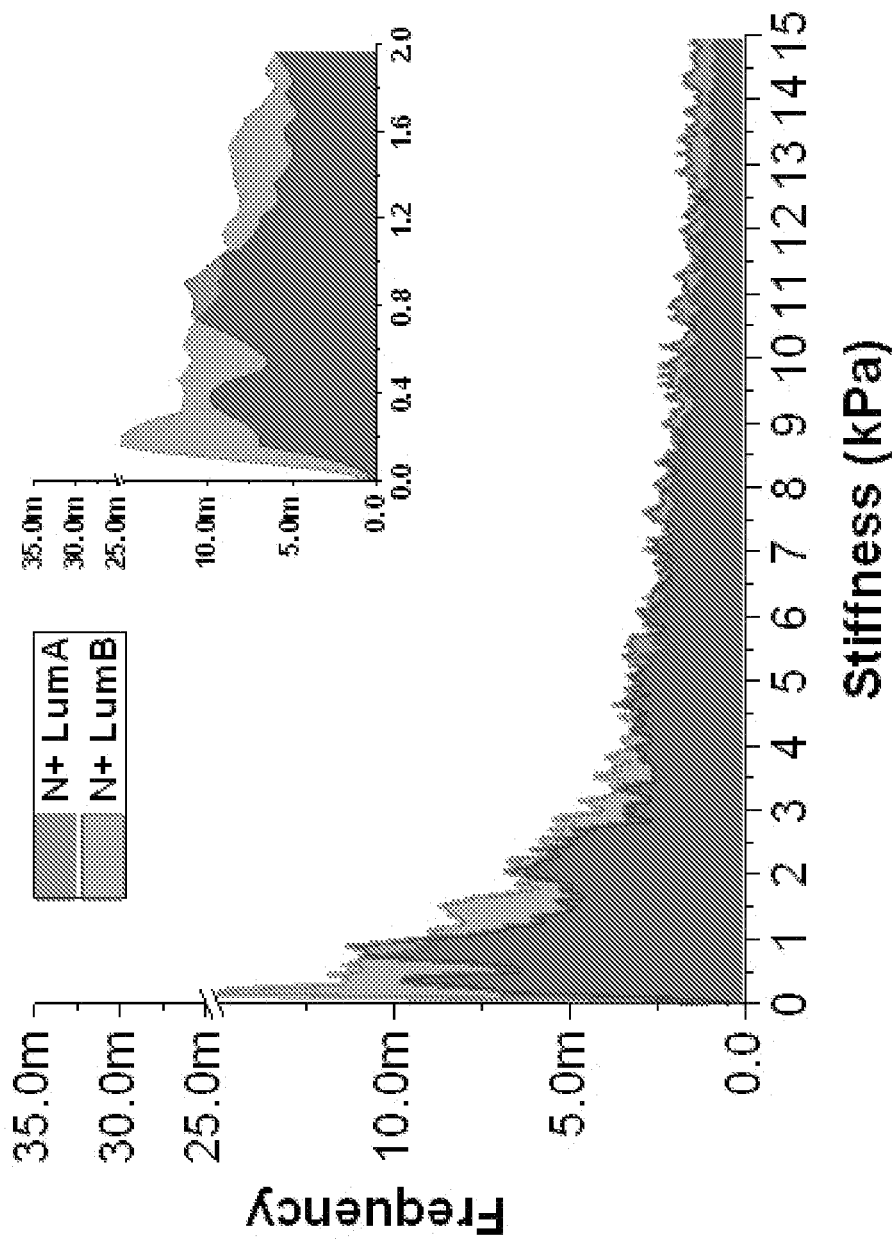

FIG. 7 shows normalized histograms representing the nanomechanical profile of the mammary tumours (biopsy samples) of N+ LumA (n=3) and LumB (n=7) patients. Within N+ patients, LumA patients show a more heterogeneous distribution than LumB patients. The cancer area in LumB patients is much softer than in LumA patients, with a broad peak around 0.2 kPa, whereas the LumA part is bimodal with peaks at 0.375 kPa and 0.875 kPa.

Figure 8:
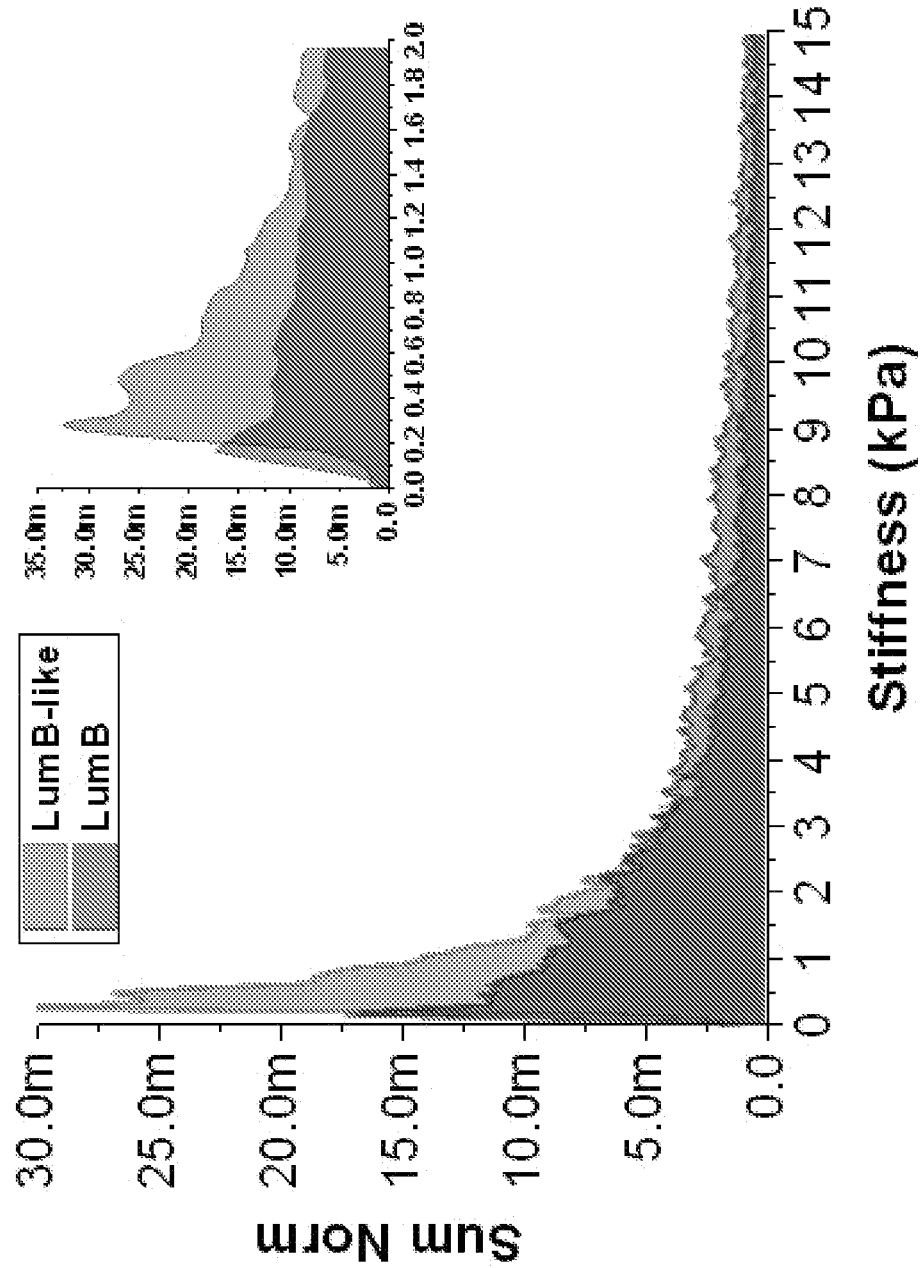

FIG. 8 shows normalized histograms representing the nanomechanical profile of the mammary tumours (biopsy samples) of N+: Luminal B (n=7) and Her2+ Luminal B-like (n=2) patients. Generally, the distribution below 2 kPa is stiffer in LumB-like patients then in LumB (Her2−) patients. The cancer area in LumB (Her2−) peaks at 0.2 kPa, in the case of LumB-like (Her2+) it peaks slightly stiffer around 0.3 kPa.

Figure 9:
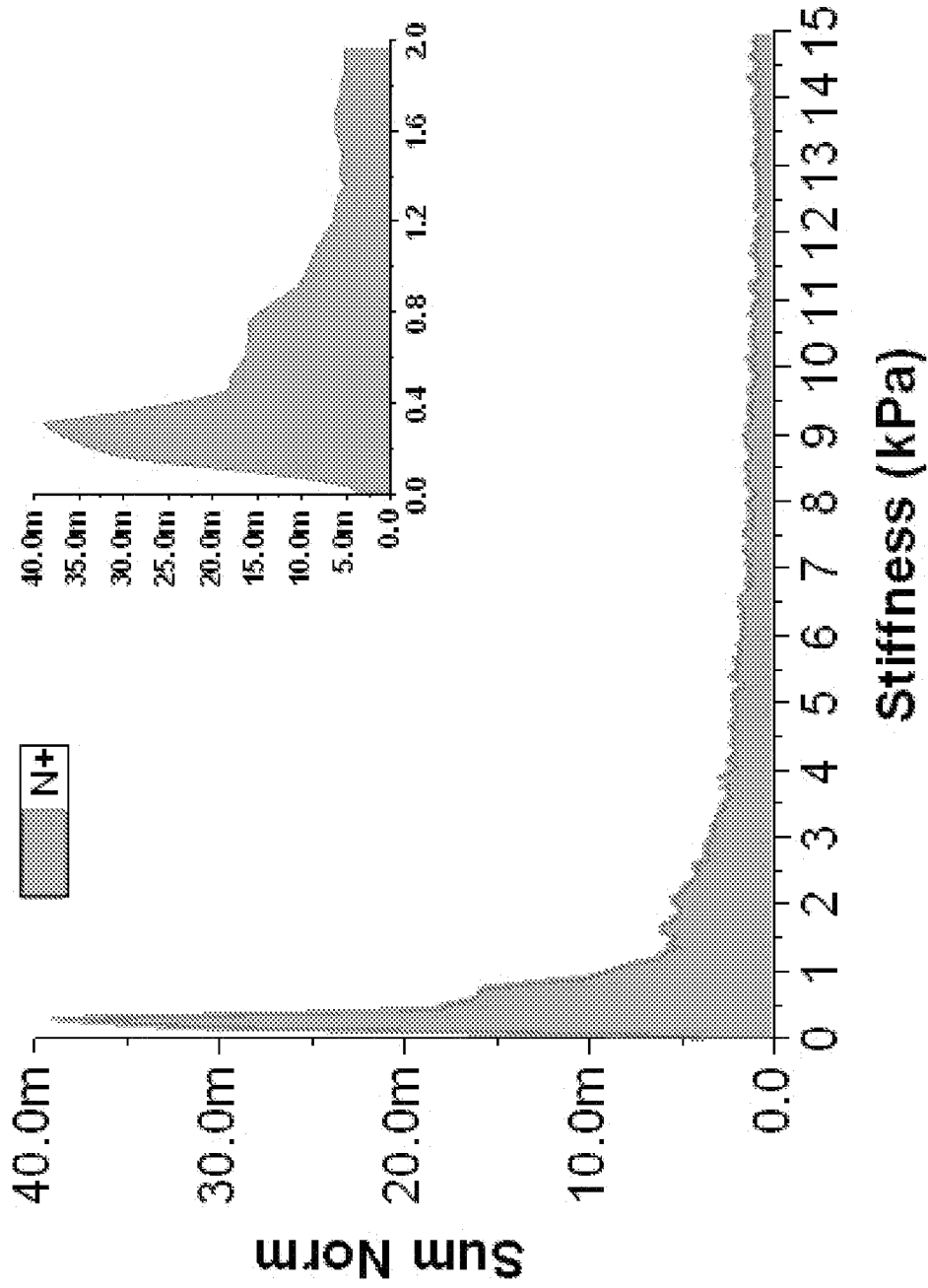

FIG. 9 shows normalized histograms representing the nanomechanical profile of invaded or cancer positive (N+) lymph nodes (biopsy samples). Cancer cell positive (N+) lymph nodes have a strong, soft peak around 0.4 kPa.

Figure 10:
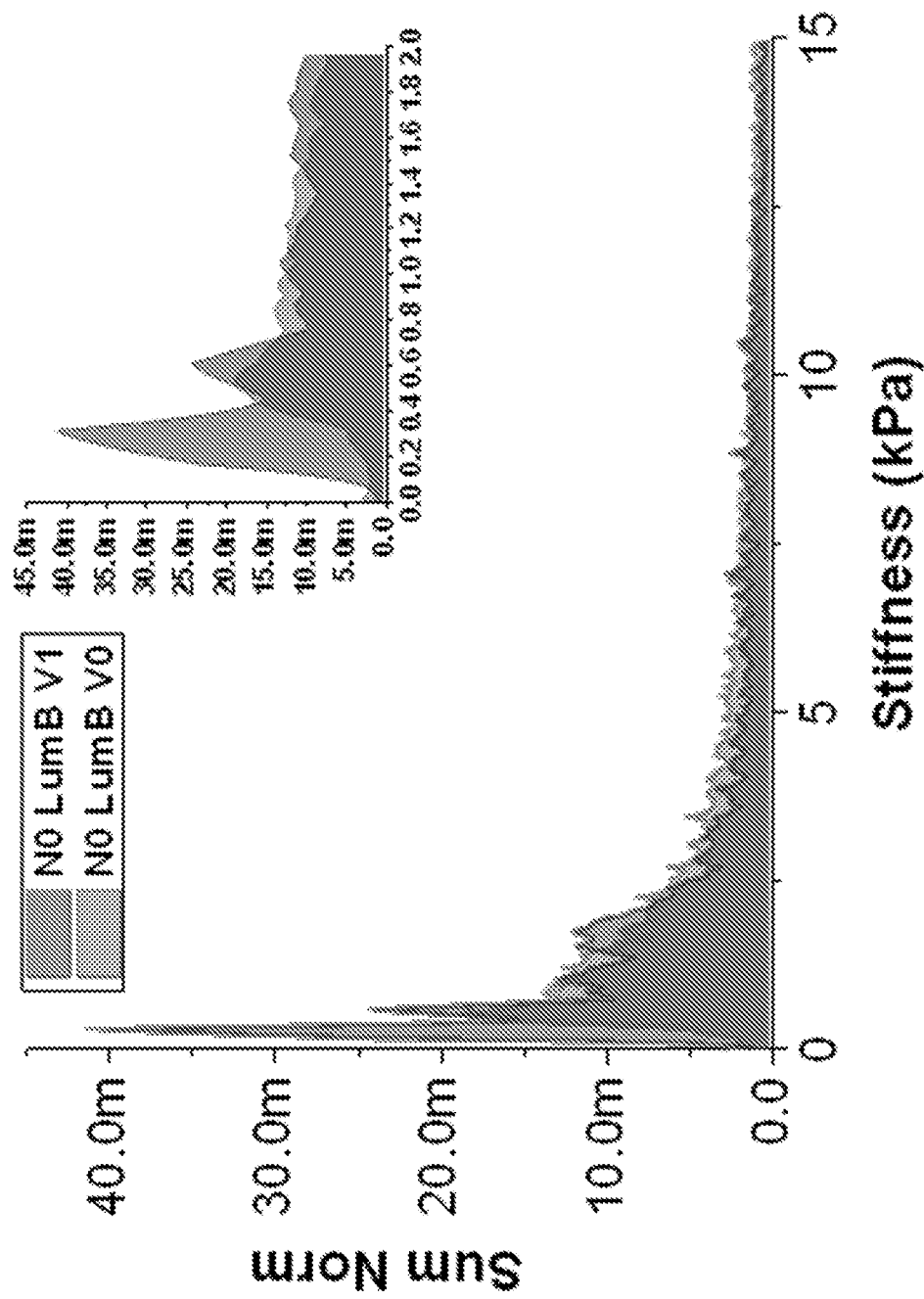

FIG. 10 shows normalized histograms representing the nanomechanical profile of the mammary tumours (biopsy samples) of LumB N0; V0 (n=3) vs V1 (n=1) patient. V1: Diagnostic features show invasion into vascular system, but no signs of distant metastasis present (at time of operation). The V1 sample shows a distinct additional soft peak around 0.3 kPa.

FIG. 11 shows an overview of the characteristic of certain breast cancer molecular subtypes.

EXAMPLES

The ARTIDIS technology ("Automated and Reliable Tissue Diagnostics"; U.S. Pat. No. 8,756,711 B2, US 2014338073 A1, WO 2014090971 A1, WO 2015001119 A1, WO 2015018865 A1 incorporated herein by reference) was optimized for analysis and subtyping of unfixed (measured in physiological aqueous environment or frozen tissue) human breast cancer samples obtained by tumour resections or biopsies. Lasting ~2 hours, an ARTIDIS assay uses a ~10 nm-sharp stylus or tip that makes ~10'000 miniscule indentations across a biopsy surface.

For this purpose, tissue samples from mammary carcinoma of various subtypes and stages were collected by biopsy or by resection from 26 patients. Typically, the collected biopsy samples had a cylindrical shape of 0.5 cm to 1.5 cm length and 1 mm to 2 mm in diameter. 10 to 20 maps are measured equidistantly on the sample, giving rise to spacing's ranging from 250 μm to 1500 μm. The size of the map ranges from 20×20 μm to 40×40 μm and contains usually 1024 measure points. Hence, 10×1024 to 20×1024 measurements are taken on a specimen.

Resections were usually 5×5 mm wide and long and with 4×4 maps giving rise to a spacing of 1 mm on average.

Nanomechanical measurements of the samples were performed as disclosed in U.S. Pat. No. 8,756,711 B2. Briefly, each sample was examined in a systematic manner by homogeneously distributing FV maps over the whole sample surface to account for possible heterogeneities. A regular distance of approximately 500 μm was kept between the scan using either micrometer screws or automated positioning systems. This resulted in roughly 10 to 15 FV maps per specimen depending on the total biopsy size.

For the analysis of the samples by AFM, biopsies were glued onto a culture dish using 2-component 5-minute fast drying epoxy glue. After a pre-drying step of 2 minutes (to avoid mixing of the epoxy and the specimen buffer), the specimen was laid flat onto the glue in order to optimize the indentation angle and to avoid influence from external components (e.g. the cantilever holder). Pipette tips acting as "ramps" were placed directly under uneven segments of each specimen to maintain height consistency. The use of excessive force (e.g. tearing or stretching) was minimized at all times during specimen handling. All preparative steps were performed in either a sterile buffer environment supplemented with protease inhibitors or transplantation buffer to prevent contamination and to ensuring that the specimen remained in a close-to-in-vivo state. The mounted specimens were kept in ice-cold Ringer's solution or Custodiol until nanomechanical testing, which was performed at room temperature or at 37° C.

For sharp pyramidal tips (205-µm-long silicon nitride cantilevers, nominal cantilever spring constant k=0.06 N m$^{-1}$, resonance frequency [air]=18 kHz), the exact spring constant k of the cantilever was determined prior to every experiment with the thermal tune method while the deflection sensitivity was determined in fluid using solid glass substrates as an infinitely stiff reference material.

Contact stiffness (elastic modulus, E) measurements of biopsies were derived as follows; load-displacement curves, also designated as force indentation curves, were recorded at a given site in an oriented manner during both loading and unloading. A regular distance of approximately 500 µm was kept between the scan regions using either micrometer screws or automated positioning systems. An individual set of data consisted of 1,024 load-displacement curves, at an indentation speed of 16 µm/s. This resulted in roughly 15 to 20 force volume maps per sample. When possible, force-volume maps (FV) were made over a 32×32 point grid with a scan size of 20×20 µm at a rate of approx. 1 load and unload cycles per second. Each load-displacement curve consisted of at least 512 data points whereas the Z length was set to 5 µm to 8 µm depending on the properties of the analyzed region. Each FV map was set to 20×20 µm$^2$ in order to (i) optimize experimental time as well as (ii) to provide a sufficiently large area incorporating all components within the tissue (e.g., cells and extracellular matrix). The maximum applied loading force was set to 1.8 nN and an indentation depth of approximately 150 to 3000 nm. Additional 72×72 FV maps (5184 force-displacement curves per map and a pixel size of 277 nm) were obtained to increase the spatial resolution over key areas of interest.

Force indentation curves were analyzed using a method described previously (Loparic, et al., *Biophysical Journal*, 98(11): p. 2731-40, 2010, Plodinec, et al., *Journal of Structural Biology*, 174(3): p. 476-484, 2011). Briefly, software was developed in LabVIEW (National Instrument, US) for the automated analysis of the FV data. The contact point was determined. Force curves were obtained transforming from piezo displacement to tip-sample distance, which accounts for the bending of the cantilever and by multiplying cantilever deflection d with the spring constant k to obtain the load F. Unloading force curves were analyzed by performing a linear fit to the upper 50% of the force curve, which defines the stiffness between the maximum load F=1.8 nN and a load of 0.9 nN. Extraneous effects on the force curve such as adhesion could be avoided by this procedure. The Poisson ratio was set to 0.5. The Young's modulus was determined according to the Oliver and Pharr method (Oliver et al., *Journal of Materials Research*, 7(6), 1564-1583, 1992). The stiffness values were spatially plotted, analyzed and displayed in ARTIDIS OFFLINE SOFTWARE.

Typically, 10,000 to 20,000 force curves were measured per sample, which were distributed in force maps of 1000 force curves homogeneously across the whole sample.

The data presented herein demonstrate applicability of nanomechanical profiling using ARTIDIS in clinics for:
1) Prognosis of cancer progression and recurrence
2) Prediction of the treatment response
3) Deciding on the appropriate treatment and follow up regimen based on the nanomechanical profile of the mammary tumour.

The nanomechanical profiling method of the invention is ideally suited for use in daily practice as it allows fast, on-site assessment of specimen and does not suffer from inter-observer variability as for example other markers, such as Ki-67.

The invention claimed is:

1. A method for classifying a tissue sample obtained from a mammary tumour, said method comprising
   determining a stiffness value for each of a plurality of points on said tissue sample using a device for determining stiffness values, resulting in a stiffness distribution, and
assigning said sample to a breast cancer molecular subtype based on said stiffness distribution, wherein said breast cancer molecular subtype is selected from
   luminal A subtype non-metastasized breast cancer,
   luminal B subtype non-metastasized breast cancer,
   luminal A subtype metastasized breast cancer,
   luminal B subtype metastasized breast cancer,
   luminal B like Her2+ subtype metastasized breast cancer,
   basal subtype non-metastasized breast cancer, and
   basal subtype metastasized breast cancer,
wherein
   a high probability of being a luminal A subtype non-metastasized breast cancer or a luminal B subtype non-metastasized breast cancer is assigned to a sample exhibiting only one frequency maximum between 0.4 kPa and 0.7 kPa in the region below 1 kPa and frequencies in the region between 1.0 kPa and 1.5 kPa, wherein said frequencies are above a threshold, and wherein said threshold equates to the half-maximal frequency of said one frequency maximum between 0.4 kPa and 0.7 kPa,
   a high probability of being a luminal A subtype metastasized breast cancer is assigned to a sample exhibiting two frequency maxima below 1 kPa and a frequency maximum above 2 kPa,
   a high probability of being a luminal B subtype metastasized breast cancer is assigned to a sample exhibiting a frequency maximum below 0.25 kPa, a high probability of being a luminal B Her2+ like subtype metastasized breast cancer is assigned to a sample exhibiting a frequency maximum between 0.25 kPa and 0.4 kPa and a frequency maximum between 1.7 kPa and 2.0 kPa,
   a high probability of being a basal subtype non-metastasized breast cancer is assigned to a sample exhibiting only one frequency maxima between 0.5 kPa and 0.7 kPa in the region below 1 kPa and frequencies in the region between 1.0 kPa and 1.5 kPa, wherein said frequencies are below a threshold, and wherein said threshold equates to the half-maximal frequency of said one frequency maximum between 0.5 kPa and 0.7 kPa,
   a high probability of being a basal subtype metastasized breast cancer is assigned to a sample exhibiting two frequency maxima below 1 kPa and that is further characterized by the absence of further frequency maxima above 1.3 kPa, and/or a high probability of being a luminal B subtype metastasized breast cancer is assigned to a sample exhibiting two frequency maxima below 1 kPa and a frequency maximum between 1.4 kPa and 2.0 kPa.

2. The method according to claim 1, wherein a high probability of being a luminal A subtype metastasized breast cancer is assigned to a sample exhibiting frequency maxima between 0.3 kPa and 0.9 kPa and/or a frequency maximum between 2.0 kPa and 2.5 kPa.

3. The method according to claim 1, wherein a high probability of being a luminal A subtype metastasized breast cancer is assigned to a sample exhibiting frequency maxima at 0.375 kPa, 0.875 kPa and 2.075 kPa.

4. The method according to claim 1, wherein a high probability of being a luminal B like Her2+ subtype metastasized breast cancer is assigned to a sample exhibiting a frequency maximum at 0.3 kPa and a frequency maximum between 1.7 kPa and 2.0 kPa.

5. The method according to claim 1, wherein said pluralities of points are determined with a spatial resolution of at least 100 µm.

6. The method according to claim 1, wherein said tissue sample is a tissue biopsy sample or a resection specimen.

7. The method according to claim 1, wherein said plurality of points is arranged with an area or a line.

8. The method according to claim 1, whereby said stiffness values of at least two different areas of said same sample are determined, and the distance between the geometrical centres of said areas is in the range of 100 µm to 1 mm.

9. The method according to claim 7, wherein said line extends along the longitudinal axis of said tissue sample.

10. The method according to claim 1, wherein said plurality of points is recorded within 6 minutes to 6 hours.

11. The method according to claim 1, wherein said plurality of points is recorded at a range of rates from 1000 loading cycles per second to 0.1 loading cycles per second.

12. The method according to claim 1, wherein said plurality of points is recorded with maximum loads ranging from 200 pN to 3 mN.

13. The method according to claim 1, further comprising determining a marker on or comprised within said tissue sample, wherein said marker is selected from human estrogen receptor, human progesterone receptor, HER2/neu receptor and antigen Ki-67.

14. A system for classifying a tissue sample obtained from mammary carcinoma, comprising
a device for determining stiffness values with a resolving power of at least 1 µm,
a programmed integrated circuit,
wherein
said programmed integrated circuit is equipped and designated to run a method according to claim 1.

15. Method for treating breast cancer, wherein the method comprises,
providing a tissue sample from a mammary tumour of a subject,
assigning the tissue sample to a breast cancer subtype by determining a stiffness value for each of a plurality of points on said tissue sample using a device for determining stiffness values, resulting in a stiffness distribution, and
assigning said sample to a breast cancer molecular subtype based on said stiffness distribution, and
administering a treatment to the subject based on the determined breast cancer molecular subtype.

16. The method according to claim 15, wherein
hormone therapy is administered to the subject in case of said mammary tumour has been classified as luminal A subtype non-metastasized breast cancer or luminal B subtype non-metastasized breast cancer,
chemotherapy is administered to the subject in case of said mammary tumour has been classified as basal subtype metastasized or non-metastasized breast cancer,
chemotherapy is administered to the subject in case of said mammary tumour has been classified as luminal A subtype metastasized breast cancer, luminal B subtype metastasized breast cancer, and/or
radiation therapy is administered to the subject in case of said mammary tumour has been classified as luminal A subtype metastasized breast cancer, luminal B subtype metastasized breast cancer, luminal B like Her2+ subtype metastasized breast cancer, or basal subtype metastasized breast cancer.

17. The method according to claim 16, wherein chemotherapy in combination with hormone therapy is administered to the subject in case of said mammary tumour has been classified as luminal A subtype metastasized breast cancer, luminal B subtype metastasized breast cancer.

18. The Method according to claim 1, wherein the device for determining stiffness values is one of: a scanning probe microscope, an atomic force microscope.

* * * * *